United States Patent [19]
Hodson et al.

[11] Patent Number: 5,437,271
[45] Date of Patent: Aug. 1, 1995

[54] DEAGGLOMERATORS FOR DRY POWDER INHALERS

[75] Inventors: Peter D. Hodson, Trowell; David J. Greenleaf, Loughborough, both of England

[73] Assignee: Minnesota Mining and Manufacturing Company, St. Paul, Minn.

[21] Appl. No.: 220,726

[22] Filed: Mar. 31, 1994

[51] Int. Cl.⁶ .................... A61M 15/00; A61M 16/20
[52] U.S. Cl. ................ 128/203.15; 128/203.12; 128/203.21
[58] Field of Search ............... 128/203.15, 203.12, 128/203.21

[56] References Cited

U.S. PATENT DOCUMENTS

| | | | |
|---|---|---|---|
| 2,587,215 | 2/1952 | Priestly | 128/206 |
| 3,187,748 | 6/1965 | Mitchell et al. | 128/173 |
| 3,669,113 | 6/1972 | Altounyan et al. | 128/266 |
| 3,795,244 | 3/1974 | Lax et al. | 128/203.15 |
| 3,948,264 | 4/1976 | Wilke et al. | 128/266 |
| 3,971,377 | 7/1976 | Damani | 128/266 |
| 4,046,146 | 9/1977 | Rosskamp et al. | 128/266 |
| 4,098,273 | 7/1978 | Glenn | 128/206 |
| 4,137,914 | 2/1979 | Wetterlin | 128/203 |
| 4,147,166 | 4/1979 | Hansen | 128/266 |
| 4,192,309 | 3/1980 | Poulsen | 128/203.15 |
| 4,240,418 | 12/1980 | Rosskamp et al. | 128/203.15 |
| 4,534,343 | 8/1985 | Nowacki et al. | 128/203.15 |
| 4,674,491 | 6/1987 | Brugger et al. | 128/200.14 |
| 4,796,614 | 1/1989 | Nowacki et al. | 128/200.14 |
| 4,846,168 | 7/1989 | Abiko et al. | 128/203.15 |
| 4,852,561 | 8/1989 | Sperry | 128/200.23 |
| 4,907,583 | 3/1990 | Wetterlin et al. | 128/203.15 |
| 5,040,527 | 8/1991 | Larson et al. | 128/200.23 |
| 5,069,204 | 12/1991 | Smith et al. | 128/203.15 |
| 5,111,780 | 5/1992 | Hannibal | 123/90.17 |
| 5,113,855 | 5/1992 | Newhouse | 128/203.12 |
| 5,161,524 | 11/1992 | Evans | 128/203.15 |
| 5,347,998 | 9/1994 | Hodson et al. | 128/203.12 |

FOREIGN PATENT DOCUMENTS

| | | | |
|---|---|---|---|
| 237507A1 | 9/1987 | European Pat. Off. | A61M 15/00 |
| 898649 | 6/1962 | United Kingdom . | |
| 1118341 | 7/1968 | United Kingdom | A61M 15/06 |
| 1262085 | 2/1972 | United Kingdom | A61M 15/00 |
| 1268051 | 3/1972 | United Kingdom | A61M 15/00 |
| 1478138 | 6/1974 | United Kingdom | A61M 15/00 |
| 1479283 | 7/1977 | United Kingdom | A61M 15/00 |
| 1526303 | 9/1978 | United Kingdom | A61M 15/00 |
| 2041763 | 9/1980 | United Kingdom | A61M 15/00 |
| 2061735 | 5/1981 | United Kingdom | A61M 15/00 |
| 2104393 | 3/1983 | United Kingdom | A61M 11/00 |
| 2165159 | 4/1986 | United Kingdom | A61M 15/00 |
| 2191718 | 12/1987 | United Kingdom | A61M 15/00 |
| 2228873 | 9/1990 | United Kingdom | A61M 15/00 |
| WO90/00670 | 1/1990 | WIPO | F01L 1/34 |
| WO90/07351 | 7/1990 | WIPO | A61M 13/00 |
| WO90/13327 | 11/1990 | WIPO | A61M 15/00 |
| 9210228 | 6/1992 | WIPO | 128/203.12 |
| WO93/09832 | 5/1993 | WIPO | A61M 15/00 |

Primary Examiner—Edgar S. Burr
Assistant Examiner—William J. Deane, Jr.
Attorney, Agent, or Firm—Gary L. Griswold; Walter N. Kirn; Dale E. Hulse

[57] ABSTRACT

A deagglomerator that defines a channel for passage of powder laden air, which channel changes its geometry in response to changing inhalation flow rate.

4 Claims, 3 Drawing Sheets

DEAGGLOMERATORS FOR DRY POWDER INHALERS

FIELD OF THE INVENTION

This invention relates to deagglomerators for dry powder inhalers and in particular to deagglomerators capable of providing effective deagglomeration over a wide range of inhalation flow rates.

DESCRIPTION OF THE RELATED ART

Asthma and other respiratory diseases have long been treated by inhalation of medicament. For many years, the two most widely used and convenient choices of treatment have been inhalation of medicament from a drug solution or suspension in an aerosol propellant from a metered dose pressurized inhaler, or inhalation of powdered drug generally admixed with a powdered excipient, from a dry powder inhaler. With growing concern being voiced over the strong link between chlorofluorocarbon emissions and depletion of the earth's ozone layer, use of chlorofluorocarbons as aerosol propellants in pressurized inhalers is being questioned and interest in dry powder systems has been stimulated.

Most single and multiple dose dry powder inhalers use either individual premeasured doses of medicament which are inserted into a dispensing chamber prior to use, or they incorporate a bulk powder reservoir from which successive quantities of medicament are transferred to the dispensing chamber. Such inhalers generally comprise an air passage leading from the dispensing chamber and terminating in a patient port adapted to be inserted into the mouth or nasal passage of the patient. Inhalation at the patient port generates an air stream through the dispensing chamber which carries particles of medicament into the lungs of the patient.

Examples of such dry powder inhalers are disclosed in U.S. Pat. Nos. 2,587,215, 3,669,113, 3,948,264, 3,971,377, 4,046,146, 4,098,273, 4,137,914, 4,147,166, 4,192,309, 4,240,418, 4,674,491, 4,846,168; British Patent Nos. 1118341, 1268051, 1526303, 2041763, 2061735, 2165159, and 2191718; European Patent No. 237507 and International Patent No. WO 90/07351.

A problem common to many dry powder systems is the tendency of the powdered medicament to agglomerate. Agglomeration is caused by individual particles of medicament adhering together in a semirigid mass, and requires an increased inspiratory effort by the patient to separate and entrain drug particles into the air stream. If the patient is unable to provide sufficient inspiratory effort the extent of drug penetration into the lower airways of the lung will be reduced. Larger agglomerated drug particles ($>10$ $\mu$m), which result from inefficient aerosolization, are not stably entrained into the patient's air stream and prematurely deposit in the mouth/throat region. Unwanted systemic side effects can occur, especially when potent drugs are administered.

It is desirable to utilize the action of the patient's breathing both to deagglomerate and to aerosolize the powdered drug, thereby overcoming the coordination problems necessary to synchronize inhalation with means for medicament aerosolization. This, however, causes the efficiency of powder aerosolization to be solely determined by the patient's inspiratory effort. Consequently, a patient having difficulty breathing, e.g., during an asthma attack, may possess insufficient inspiratory effort to deagglomerate/aerosolize and inhale the required dose of medicament at a time when the patient has the greatest need for the drug.

Many inhalation devices have attempted to solve the problems attributable to powder agglomeration by incorporating into the device deagglomeration and aerosolization means, e.g., a battery-powered solenoid buzzer, which cause or assist deagglomeration and/or aerosolization of the powdered medicament by making the degree of break up of particle agglomerates entirely independent of the strength of the patient's inspiratory effort. Examples of such devices are disclosed in, e.g., U.S. Pat. Nos. 3,948,264, 3,971,377 and 4,147,166. The device can be made fully independent of the patient by incorporating a breath actuation mechanism that is responsive to respiratory flow and therefore able to synchronize medicament release with patient inhalation. An example of such a device is disclosed in our copending International Patent Application No. 90/00670 filed on 30th Apr. 1990.

Dry powder inhalers are also known which incorporate features to assist the break up of particle agglomerates in a powder laden air stream. For example, British Patent No. 1268051 and U.S. Pat. No. 3,669,113 disclose dry powder inhalers in which a premetered dose of powdered medicament is contained in a capsule and the airflow past the capsule is increased in velocity by means of a constriction in the air passage. British Patent No. 2165159 discloses a dry powder inhaler with a storage chamber for powdered drug comprising a constricted region in the air passage in the mouthpiece region.

British Patent Nos. 1478138, 1526303 and 2061735 and U.S. Pat. Nos. 3,948,264, 4,046,146, 4,137,914, 4,240,418 and 4,846,168 disclose dry powder inhalers having an angled mouthpiece which forces the powder laden air stream to pass around a bend.

U.S. Pat. Nos. 2,587,215 and 4,674,491 and International Patent No. WO 90/07351 disclose dry powder inhalers in which a powder laden air stream is forced to take a fairly tortuous path prior to exiting the mouthpiece. British Patent Nos. 1118341 and 2191718 and European Patent No. 237507 disclose dry powder inhalers in which the particle laden airstream is forced to pass round interdigitated baffles or the like in the mouthpiece region.

Our co-pending PCT Application claiming priority from British Patent Application No. 9123953.3 discloses a dry powder inhaler for dispensing powdered medicament comprising a housing defining a chamber for receiving a dose of powdered medicament, one or more air inlets and a patient port adapted for insertion into the mouth or nasal passage of the patient, constructed and arranged to provide an air passage extending from the air inlet(s) through the chamber to the patient port so that patient inhalation at the patient port generates an airflow through the inhaler which entrains particles of medicament from the chamber for inhalation by the patient, and in which the air passage is provided with one or more deagglomeration channels between the chamber and patient through which the airstream with entrained medicament must pass, each channel having a substantially constant cross-sectional profile with a cross-sectional area no greater than 40 mm$^2$, a first opening communicating with the dispensing chamber, a second opening communicating with the patient port and intermediate of said first and second openings either:

(i) a single bend of from 70 to 160° wherein the minimum radius of curvature of the center of the bend is no greater than 10 mm, or (ii) two or more bends each of from 35 to 200°, wherein the minimum radius of curvature of the center of the bends is no greater than 10 mm.

This deagglomerator utilizes one or more shaped and dimensioned channels to confine the powder carrying airstream leaving the dispensing chamber, thereby imparting shear and wall friction forces to the particles. These forces break up particle agglomerates into smaller particles which are capable of being inhaled into the human lung. The cross-sectional profile and dimensions of the deagglomeration channel(s) are selected so as to maximize the delivery of particles of respirable size (2 to 5 μm) over the whole range of likely inhalation rates, while minimizing factors such as drug deposition. It has been found that a channel of substantially constant cross-sectional profile of up to 40 mm² (inclusive), imparts enough shear and wall friction forces to promote the deagglomeration of entrained powder agglomerates.

Deagglomerators of fixed geometry tend to show flow rate dependence of respirable fraction (the fraction of total mass of drug powder which is capable of getting into the lungs) and sometimes also of delivered dose. The underlying reason for this is that higher inspiratory airflow rates tend to lead to greater pressure drops through such deagglomerators, hence giving rise to more turbulence and shear of the powder laden airflow. More energy is thus available to break up particle agglomerates.

The pressure drop versus flow rate curve will depend upon the construction of the deagglomerator. A deagglomerator with a high resistance to airflow will produce a curve which increases rapidly with flow rate, while a deagglomerator with wide channels having a low resistance to airflow will produce a shallow curve. While the latter construction will provide greater patient comfort it will have a poorer deagglomeration performance, particularly at lower flow rates.

In practice it is not readily possible to design a device which gives a consistent degree of powder deagglomeration over a wide range of flow rates. In theory one can make the deagglomerator so efficient that the respirable fraction essentially "saturates" (i.e., RF=100%) at the lowest flow rate at which the device is likely to be used. For example, if the sonic limit of air velocity is reached, the velocity and thus the deagglomeration and respirable fraction will "saturate". Unfortunately, because of the nature of the curve of pressure drop against flow rate any known type of deagglomerator able to do this would have an extremely high inspiratory resistance at higher flow rates and would be extremely uncomfortable for the patient to inhale through and would not be suitable for use by an asthmatic or patient with other breathing difficulties.

One way of achieving more consistent deagglomeration is to utilize a source of energy independent of the patient's inspiration. For example, an impaction device or blast of compressed gas may be employed to deagglomerate and project the powder in the inspiratory airflow.

Although various forms of valves and impellers have been employed in conjunction with deagglomerators in known devices there is no known deagglomerator which changes the passage of the flow of powder laden air in response to increasing airflow rate to control the pressure drop. For example, British Patent Nos. 898649 and 1479283 and European Patent No. 470154 disclose a dry powder inhaler in which a valve means is provided which opens solely upon inhalation by the patient, said opening allowing the powder aerosol to be released only when an adequate airflow rate has been attained.

British Patent No. 1118341 discloses a dry powder inhaler embodiment comprising a nonreturn valve in the mouthpiece featuring a floating disk with a hole in it, said disk being capable of moving relative to another disk with holes near its periphery in response to the direction of the patient's airflow.

British Patent No. 2104393 discloses a metered dose inhaler for pressurized formulations in which a valve at the air inlet closes off much of the airflow through the device prior to manual discharge of a dose of medicament by the patient.

U.S. Pat. No. 5,040,527 discloses a spray dispenser apparatus with a two position air inlet valve which allows a higher flow rate of air to mix with the spray to be inhaled only when a metered dose inhaler unit is operated. The change in geometry of the valve is not caused by the airflow increasing, and the airflow channel traversed by the spray is not changed in geometry.

British Patent No. 1262085 discloses a dry powder inhaler comprising a propeller arranged to rotate and precess during inhalation through the device. While the rotation does not alter the air channel geometry (although it rotates the effective air channel), the wobbling motion will affect the channel geometry very slightly if the off-axis angle varies. In practice, however, the off-axis angle maintains its maximum value at all but the very lowest flow rates, and in any case the effective channel geometry change is too small to have a significant effect on the powder aerosol.

U.S. Pat. No. 5,161,524 discloses a breath actuated inhalator having a primary and a secondary airflow conduit wherein regulator means are provided in the secondary airflow conduit to planate maximum airflow velocity through the inhaler. By optimizing airflow and velocity rate, the breath actuated inhalator prevents problems associated with excessive inhalation velocity such as dry powder drug compound impingement upon the outside radius of the throat. Only the airflow through the primary airflow conduit carries the dry powder drug compound.

SUMMARY OF THE INVENTION

The present invention provides an alternative approach in which the deagglomerator is designed to compensate for changing airflow.

Therefore according to the present invention there is provided a deagglomerator for breaking up powder agglomerates in an air stream, comprising a housing defining a channel for passage of powder laden air, the channel communicating between an aerosol source and a patient port and being configured to cause significant deagglomeration of agglomerated powder, characterized in that the deagglomerator additionally comprises means to change the geometry of said channel in response to varying inhalation rate.

The invention provides a variable geometry deagglomerator, preferably for use with a dry powder inhaler, in which the geometry is automatically changed in response to varying inhalation rate by the patient in such a way as to tend to reduce the airflow rate dependence of the delivered dose and/or respirable fraction of the inhaled powder aerosol. The invention extends to deagglomerators having a channel comprising one or more individual passages whose intrinsic geometries change with inhalation rate, e.g., by variation of cross section or mean path length, and deagglomerators having a channel comprising a plurality of individual passages of which the number exposed to the powder laden air varies with inhalation rates. These changes of geometry may be caused directly by the airflow or may be caused by some "intelligent" sensor or logic driven controller.

The deagglomerators of the invention respond to increasing flow rates to vary the geometry of a channel through which the powder laden air passes in a manner that results in a lesser pressure drop increase than would be seen in the absence of the variable geometry. Thus, significant control of the pressure drop is exercised and flow rate dependence of deagglomeration efficiency is reduced without affecting deagglomeration efficiency. It will be appreciated the variable geometry of the deagglomerators affects the flow of powder laden air and does not function as a bypass valve diverting airflow past the deagglomerator.

BRIEF DESCRIPTION OF THE DRAWINGS

The invention will now be described with reference to the accompanying drawings in which.

DESCRIPTION OF THE PREFERRED EMBODIMENTS

Figure 1:
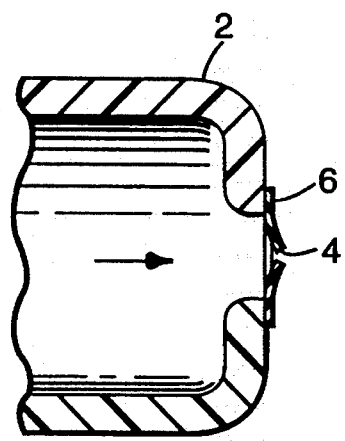
FIG. 1 is a diagrammatic section through a deagglomerator in accordance with the invention.

FIG. 1 shows an example of a deagglomerator of the present invention with an intrinsic geometry change caused by the airflow rate increasing. Air laden with powder agglomerates moves in the direction of the arrow as the patient inhales through the patient port, i.e., mouthpiece (2). At low airflow rates the slit (4) in the rubber diaphragm (6) opens slightly to let the air through. The pressure drop and turbulence which the air experiences as it traverses the slit region cause deagglomeration. At higher airflow rates the slit bulges further open, thus preventing the pressure drop rising too high.

Figure 2:
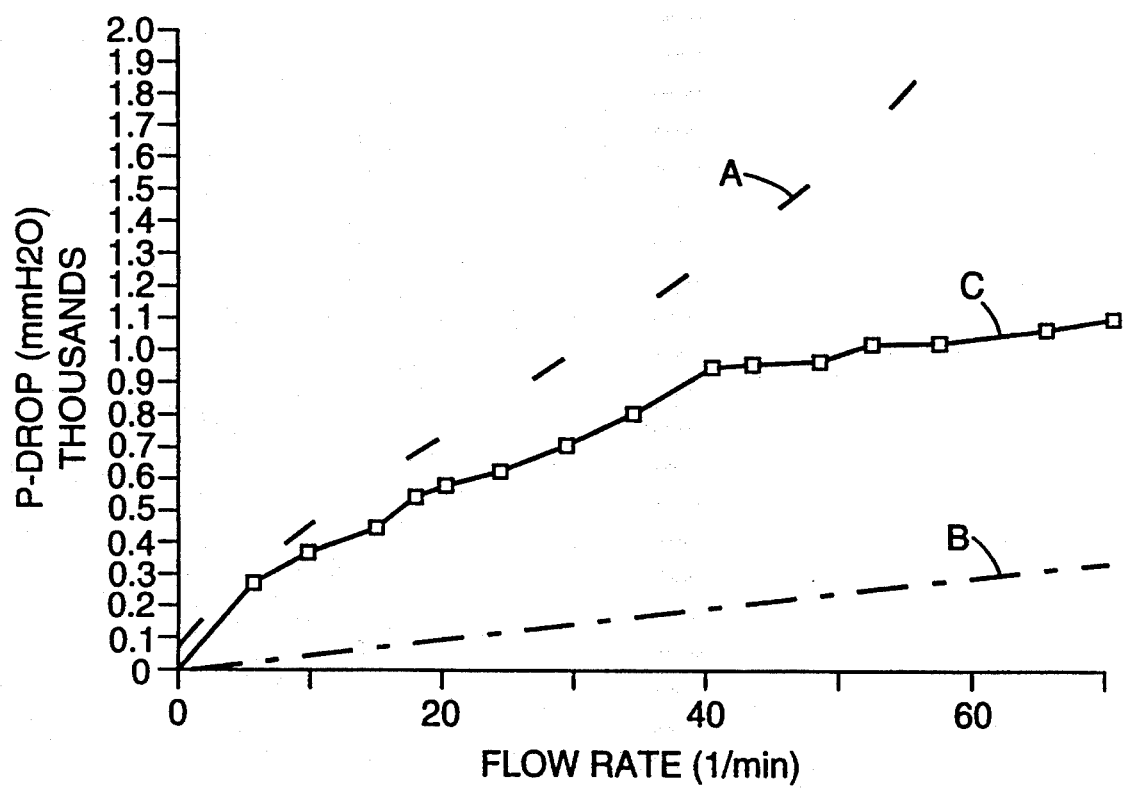
FIG. 2 is a plot of pressure drop versus airflow rate for three deagglomerators.

FIG. 2 represents plots of pressure drop against flow rate for various deagglomerators. Curve A is representative of a fixed geometry deagglomerator having a relatively high resistance to airflow, the curve increasing rapidly with flow rate. Curve B is representative of a fixed geometry deagglomerator of low resistance to airflow, but typically with poorer deagglomeration performance. Curve C is representative of the deagglomerator in accordance with the invention as shown in FIG. 1. Curve C shows how the pressure drop varies with flow rate for a slit 10.9 mm long in a 250 μm thick rubber diaphragm. The shape of the curve is clearly different to Curves A and B and the pressure drop at 60 l/min is less than 1.6 times that at 30 l/min. Instead of a slit in a rubber diaphragm, a gap below the end of a weighted or spring-resisted vane may form the deagglomerator.

Figure 3:
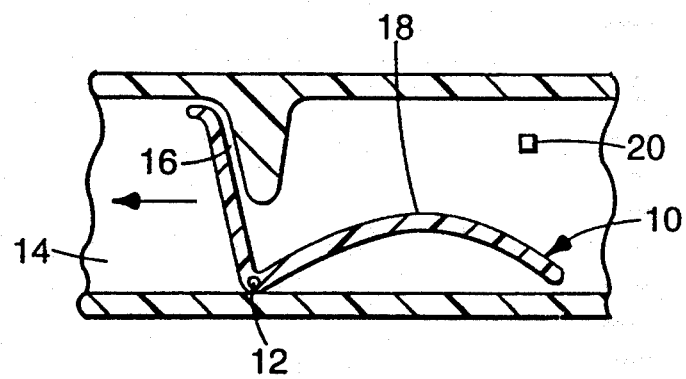
FIGS. 3 and 4 are diagrammatic sections through deagglomerators in accordance with the invention.

FIG. 3 shows an alternative embodiment of a deagglomerator of the present invention with a geometry change caused by changes in the airflow rate. A vane (10) is pivoted at point (12) in the airflow channel (14) which has a rectangular cross section. At low flow rates the gap (16) is narrow, causing a high pressure drop and sufficient turbulence to adequately deagglomerate the powder aerosol. As the airflow rate increases, however, the air velocity above surface (18) rises sufficiently to cause the vane to pivot counterclockwise about point (12) due to the Bernoulli effect. This rotation widens the gap (16), preventing the pressure drop or turbulence rising excessively, and causing the respirable fraction to be far less dependent on airflow rate than it would otherwise be. A stop (20) prevents the curved surface (18) reaching the roof of the channel. Alternatively, the surface (18) may have an aperture in it (not shown) to prevent it blocking the channel if it reaches the roof of the channel. A spring could be used, rather than gravity, to bias the vane in a clockwise direction, thereby making the system independent of gravity.

Figure 4:
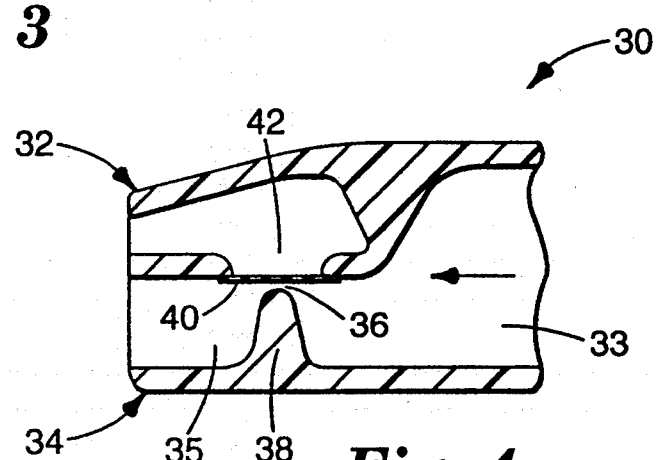

FIG. 4 shows a further embodiment with a geometry change caused by changes in the patient's inspiratory effort. The mouthpiece (30) comprises two parts (32 and 34), which are inserted into the mouth together. At low airflow rates, the air and powder stream through the channel (33, 36, 35), is forced to pass through the narrow gap (36) between protrusion (38) and the thin diaphragm (40), which seals region (42) off from the airflow. This narrow gap causes turbulence in the air stream, thereby deagglomerating the powder. At higher airflow rates, however, the pressure in region (42) is reduced with respect to the pressure in region (35) as the patient inhales harder. This causes the diaphragm (40) to bow upwards, widening the gap (36). The pressure drop across the channel (between the ends of the channel), and the turbulence through it, is thus lower than it would be if the variable geometry were not variable. The respirable fraction is thus more constant with airflow rate. Alternatively, a gravity or spring biased piston could be used in place of the diaphragm.

Figure 5:
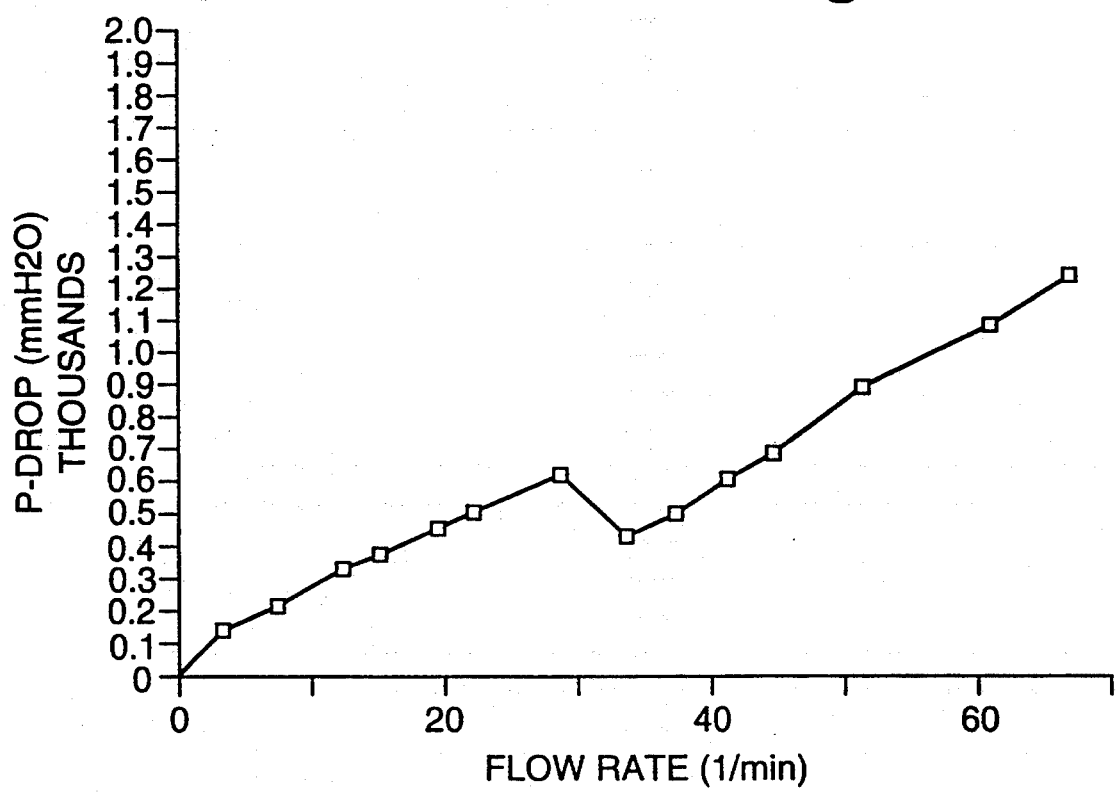
FIG. 5 is a plot of pressure drop versus airflow rate for the deagglomerator of FIG. 4.

FIG. 5 shows results from a deagglomerator of the form of FIG. 4, where there is actually negative differential resistance to airflow between 28 l/min and 34 l/min as the diaphragm bows upwards.

Figure 6A:
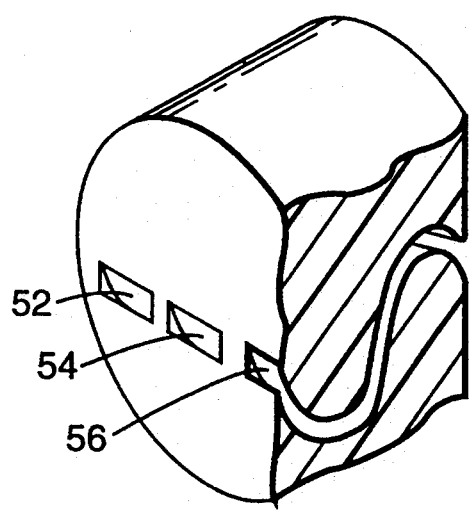
FIGS. 6(a) and (b) are diagrams of a further deagglomerator in accordance with the invention and vane for use therewith and FIG. 7 is a plot of pressure drop versus airflow rate for the deagglomerator of FIG. 6.
Figure 6B:
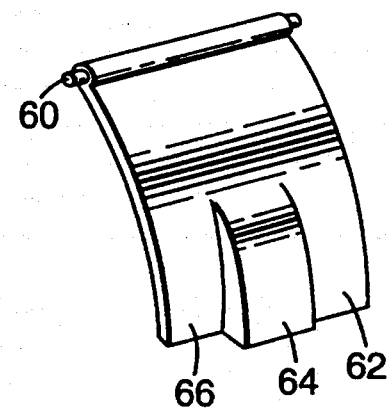
Figure 7:
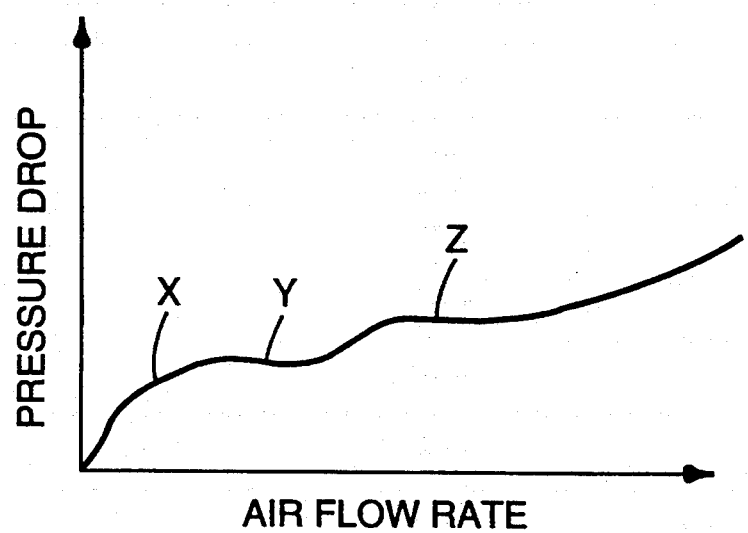

FIGS. 6(a) and (b) illustrate the principle of a further embodiment of a deagglomerator of the present invention wherein the geometry of the channel is changed by way of changing the number of individual deagglomerator passages passing the powder aerosol as the flow rate changes. The channel of the deagglomerator in FIG. 6(a) comprises three parallel passages (52, 54, 56), separate throughout their lengths, so that a powder laden airflow entering one is unable to cross into another. A vane with a form shown in FIG. 6(b) is used in conjunction with this deagglomerator and is positioned to selectively block the passages. For an indirectly breath actuated dry powder inhaler, this vane may be the vane that triggers the inhalation release mechanism.

At low flow rates, e.g., 20 liters per minute, the vane pivots about point (60) and lifts in the inhaled airstream (sufficiently to trigger the powder release mechanism if it forms part of a breath actuated mechanism) so that part (64) of the vane clears the inlet to passage (54) of the deagglomerator. If the flow rate is higher, e.g., 40 1/min, the vane lifts higher in the airflow and part (62) of the vane clears the inlet to passage (52). At still higher airflows, e.g., 60 1/min, part (66) clears passage (56). Thus at 20 1/min, the powder laden air is confined to one passage of the deagglomerator. At 40 1/min, double the flow is allowed into two passages. At 60 1/min, a treble flow is allowed into three passages. Hence by using this automatically variable geometry deagglomeration arrangement the linear speed of the powder laden air is approximately the same at 20, 40 or 60 1/min. Hence the pressure drop versus flow rate curve approximates to that shown in FIG. 7 in which X represents the stage with passage (54) open, Y represents the stage with passages (54 and 52) open and Z represents the stage with all three passages (54, 52 and 56) open. The exact curve will vary depending on the sealing tolerances between vane and deagglomerator inlets and the friction characteristics of the vane pivots etc.

This description is illustrative. Different numbers of passages may be envisaged; the vane front may be V-shaped rather than stepped; the vane front may be straight and the channel inlets may be displaced relative to each other etc. Alternatively, individual flap valves covering all or all but one of the separate passages may be employed, capable of opening each at a different flow rate. Such a system has been shown capable of displaying limited regions of negative differential resistance to airflow similar to that in FIG. 5.

The claimed invention Is:

1. A deagglomerator for breaking up powder agglomerates in an air stream, comprising:

a housing defining a channel for the passage of powder laden air and further defining a mouthpiece; and means for changing the geometry of said channel in response to varying air flow rate through said channel, said geometry changing means comprising:

a flexible membrane positioned within said housing so as to form a gap between said flexible membrane and said housing, said gap forming part of said channel, said flexible membrane being capable of flexing with increasing air flow rate through said channel so as to widen said gap; and a hollow region formed in said housing and positioned adjacent said flexible membrane, said flexible membrane sealing off said hollow region from said channel, said hollow region and said channel both having an opening at the end of said mouthpiece such that a partial vacuum is created within said hollow region when a patient inhales at the end of the mouthpiece, thereby causing said flexible membrane to bow upwardly into said hollow region and widen said gap.

2. A deagglomerator as defined in claim 1 wherein said housing further comprises a protrusion formed therein so as to obstruct part of said channel, said flexible membrane being positioned above said protrusion such that said gap is formed therebetween, said flexible membrane being capable of flexing away from said protrusion with increasing air flow rate through said channel so as to widen said gap.

3. A deagglomerator as defined in claim 1 in combination with a dry powder inhaler device.

4. A deagglomerator as defined in claim 2 in combination with a dry powder inhaler device.

* * * * *